United States Patent [19]

Mizuno

[11] Patent Number: 4,944,585

[45] Date of Patent: Jul. 31, 1990

[54] DEVICE FOR MEASURING PUPILLARY DISTANCE

[75] Inventor: Toshiaki Mizuno, Gamagori, Japan

[73] Assignee: Nidek Co., Ltd., Gamagori, Japan

[21] Appl. No.: 281,367

[22] Filed: Dec. 8, 1988

[51] Int. Cl.⁵ .............................................. A61B 3/10
[52] U.S. Cl. ..................................... 351/204; 33/200
[58] Field of Search ................... 351/204, 200; 33/200

[56] References Cited

U.S. PATENT DOCUMENTS 3,495,897  2/1970  Deforges .
4,591,246  5/1986  Cousyn et al. .

FOREIGN PATENT DOCUMENTS 59-120128  7/1984  Japan .

*Primary Examiner*—Paul M. Dzierzynski
*Attorney, Agent, or Firm*—Armstrong, Nikaido, Marmelstein, Kubovcik & Murray

[57] ABSTRACT

Since a certain relationship exists between a pupillary distance at a viewing distance and a pupillary distance to another viewing distance, the pupillary distance at a desired viewing distance can be obtained by making a predetermined correction in the results of a pupillary distance measurement at a fixed viewing distance, without requiring a convexed lens in the device to be moved. The fixed viewing distance is preferably set at a small value such as 1 to 2 meters so that problems such as failure in forming a fused image due to machine near sightedness can be avoided. The device has a sighting mark forming device which can be installed at any portion of the measuring device for enabling easy assembly, unlike conventional measuring devices which require that the sighting mark forming device is located in relation to the (corneal) vertex distance of the subject.

11 Claims, 5 Drawing Sheets

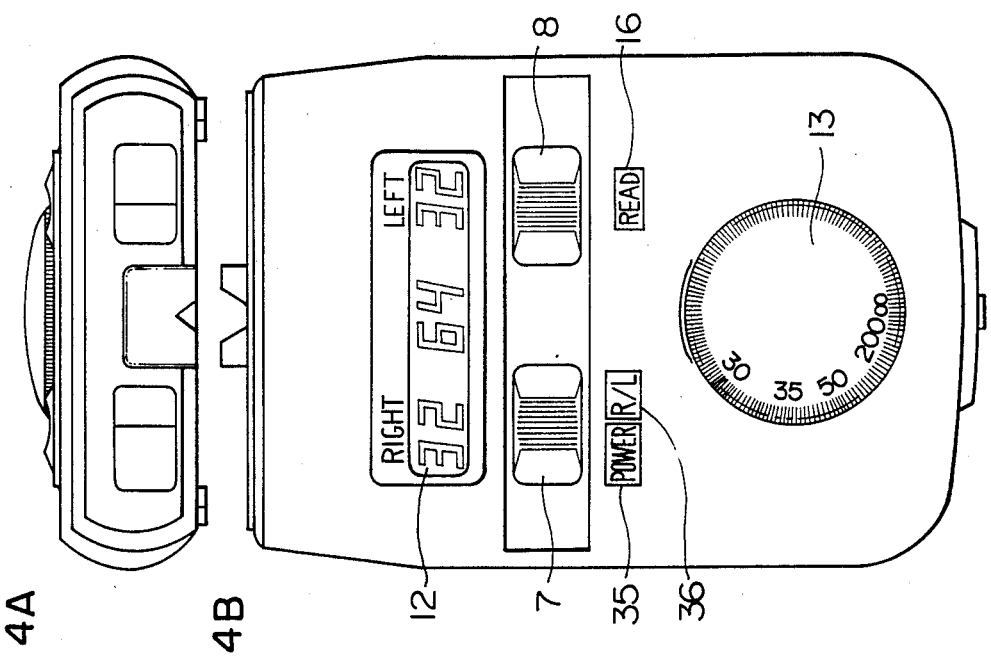
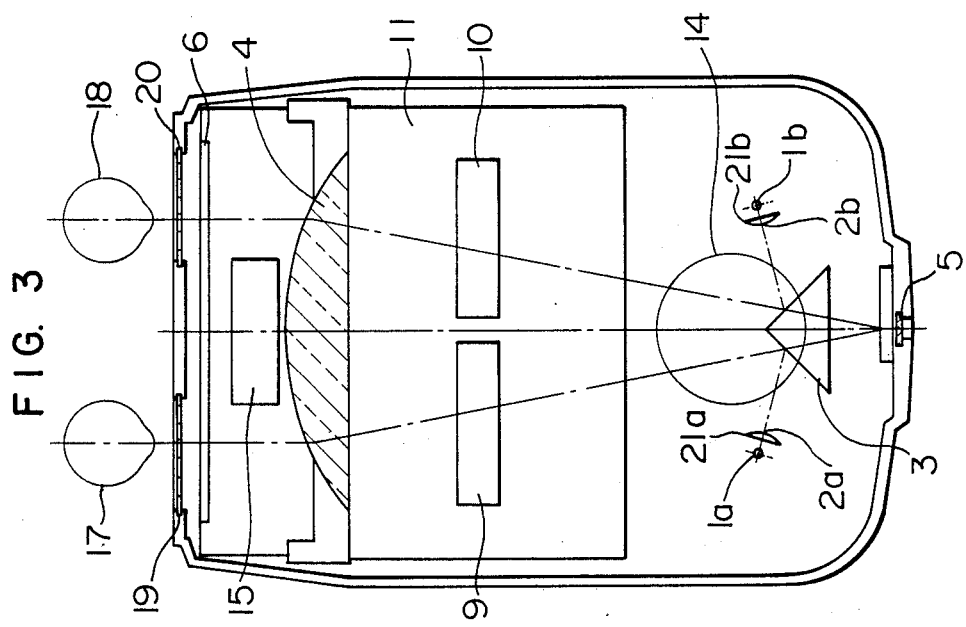

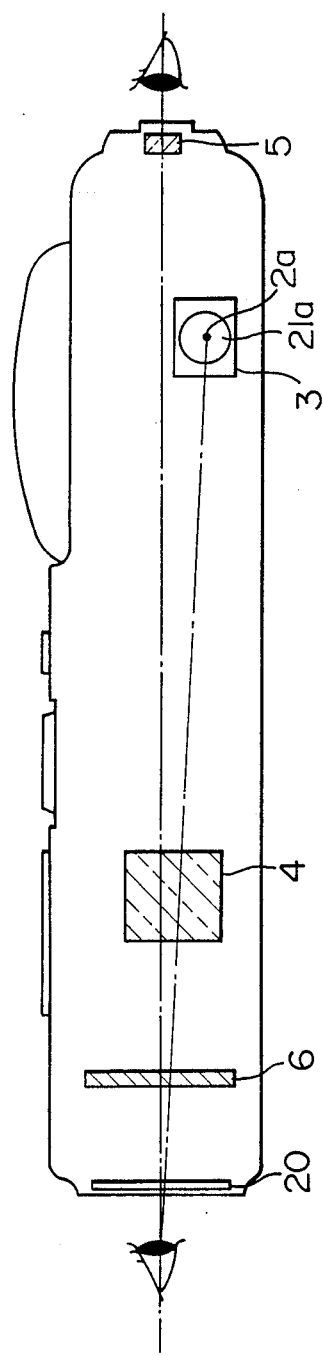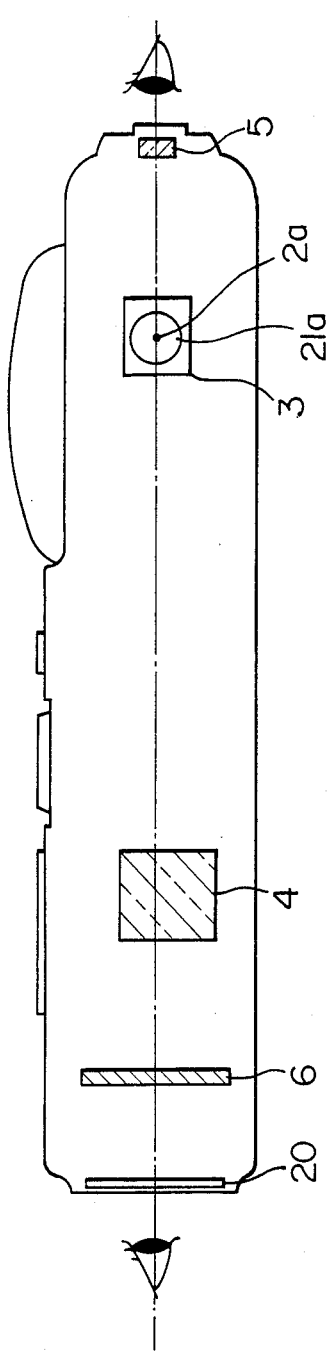

DEVICE FOR MEASURING PUPILLARY DISTANCE

BACKGROUND OF THE INVENTION

FIELD OF THE INVENTION

The present invention relates to a device for measuring pupillary distance (referred to also as PD value hereinafter) of a subject to obtain data necessary for optimumly setting a lens in a spectacle frame.

Setting of a lens in spectacles frame essentially requires that the visual axis of the subject at a viewing distance under an average state of use coincides with the optical axis of the lens. In particular, a high degree of coincidence is required in the case of a progressive lens which has recently been developed and put into use. In general, a progressive lens comprises three portions of different optical characteristics: namely, a farvision portion which is used when sighting an object which is at a long distance from the subject, a near-vision portion which is used when sighting an object which is at a short distance from the subject, and a progressive portion in which a progressive zone is an optically usable region. When sighting condition with this lens is changed from a far-vision state to a near-vision state, it is necessary that the visual axis is progressively moved from the far-vision portion to the near-vision portion, across the narrow progressive zone.

Any discrepancy between the visual axis of the subject and the optical axis of the lens causes problems such as generation of prism or failure in obtaining expected correction effect.

A typical known pupillary distance measuring device has the following construction. When the subject is made to sight at a spot light source (a fixation target), a cornea reflection image (bright spot) is formed. The position of this bright spot as viewed from the same side as the light source is defined as a vertex of cornea. The position of the vertex of cornea is regarded as the position passed by the visual axis. The distance between the vertex of the cornea and the nose of the subject is measured as the pupillary distance. The viewing distance is variable by shifting a convexed lens.

This known arrangement is disclosed in detail in the specification of the U.S. Pat. No. 3,495,897. The shifting of the convexed lens requires a linear motion mechanism including various parts such as a viewing distance setting knob, a slide guide interlocked with the knob, a connecting rod and so forth, with the result that the device as a whole is highly complicated in construction.

SUMMARY OF THE INVENTION

The known pupillary distance measuring device suffers from various other drawbacks or inconveniences.

For instance, it is necessary to set the viewing distance for each individual subject. In case of a multifocus lens which requires measurement at a plurality of viewing distances, the measurement has to be repeated from the beginning. In some cases, the subject, who has looked into the pupillary distance measuring device, falls in a temporary "machine near sightedness" state so that the fixation target at an infinite distance cannot be imaged as a fusion, with the result that the measurement cannot be conducted.

Accordingly, an object of the present invention is to overcome the above-described problems of the prior art.

To this end, according to the present invention, there is provided a device for measuring pupillary distance comprising: a sight spot forming device disposed in the device and including a light source; a window provided in a front panel of the device in such a manner as to enable a subject to look at the sight spot in the device; a locating device for locating the front panel properly in relation to the face of the subject; a converging lens fixed in the device such that the appearant viewing distance of the fixation target has a predetermined distance value and disposed corresponding to at least an eye of the subject; a sighting mark forming device provided on the inner side of the front panel such as to form a sighting mark which corresponds to the position of a cornea reflection image of the fixation target formed on the cornea of the subject; a sighting mark position control device for enabling an inspector to control the position of the sighting mark in relation to the position of the cornea reflection image; an observation device for enabling the inspector to observe the front portion of an eye of the subject; a sighting mark position reading means capable of reading the position of the sighting mark; a viewing distance setting device for setting the viewing distance at which the pupillary distance is to be determined; a computing device for computing the pupillary distance at the viewing distance set by the viewing distance setting device; and a display device for displaying the result of computation; whereby the pupillary distance at a desired viewing distance can be determined from the result of measurement of the pupillary distance at a preselected viewing distance.

In operation, after the front panel of the device are properly positioned to the subject, the subject is made to sight, through the window portion, at a fixation target which is appearantly located, by virtue of the converging lens, at a predetermined viewing distance. In this state, the inspector operates the device to move the sighting mark such that a predetermined positional relationship is established between the cornea reflection image and the sighting mark. The device then automatically reads the position of the sighting mark. Then, the inspector sets a viewing distance for the pupillary distance in question, the device computes the pupillary distance at the set viewing distance on the basis of the position of the sighting mark and displays the required pupillary distance on the display section of the device.

With the pupillary distance measuring device of the present invention, therefore, the inspector can know the pupillary distances for individual subjects, from a single predetermined viewing distance. In addition, pupillary distance data concerning pupillary distances at a plurality of viewing distances as required in the case of a progressive lens can easily be obtained simply by switching the viewing distance. Even if "machine near sightedness" has taken place, a fusion of the fixation target can be formed by operating the device so as to reduce the viewing distance, so that the required pupillary distance can be obtained. As the position of the sighting mark can be placed on a position having a voluntary distance from the vertex of cornea of the subject, it is not only easy to produce the device but also unnecessary to adjust the device for exporting, alternatively simply changing a set of the value in the computer being enough to measure.

The principle of the measurement with the device for measuring pupillary distance according to the present invention will be described hereunder.

The pupillary distance (PD value) used in spectacles dispensation in the value which is to be obtained at a position ordinarily occupied by the spectacles lens when the user or subject wears the spectacles. The distance between this lens position and the vertex of cornea is referred to as "vertex distance" and usually about 12 mm for Japanese people and about 13.75 mm for western people as standard.

The distance from the vertex of cornea to the rotation center is estimated to be about 13 mm in many papers. So that value is used in the present invention, but it is correctable on the basis of experience.

FIG. 1 illustrates the state of the subject's eye directing its visual axis towards the fixation target spaced at distance "a" (mm) in front of the eye. When the viewing target is on the visual axis, the cornea reflection image is on it, too. So the relationship between $PD\infty$ which is PD value at infinity and PDm which is PD value at distance "b" is represented by the following formula.

$$\frac{PDm}{PD_\infty} = \frac{a-b}{a+c}$$

where "c" represents the distance from the vertex of cornea to the rotation center. Assumming that the value "a" is 1000 mm, the distance "b" is 30 mm and the distance "c" is 13 mm.

$$\frac{PDm}{PD_\infty} = 0.9576$$

$$PD_\infty = 1.0443 \, PDm.$$

Then FIG. 2 illustrates the state of the eye sighting a fixation target spaced at the viewing distance L. The relationship between $PD\infty$ and the PD value (PD) at the vertex distance (VD) is as follows;

$$PD = PD_\infty \times \frac{L - VD}{L + c}$$

assuming that the "VD" is 12 mm and the "c" is 13 mm, $$PD \approx 1.0443 \, PDm \times \frac{L - 12}{L + 13}$$

Thus once PDm is measured, it's possible to obtain PD values at any viewing distance.

BRIEF DESCRIPTION OF THE DRAWINGS

FIG. 3 is a sectional view of an embodiment of the present invention;

FIG. 4A shows an appearance of an embodiment as viewed from the subject side;

FIG. 4B is a plan view of the embodiment shown in FIG. 4A;

FIG. 8 is a sectional side elevation of the embodiment according to the invention shown in FIG. 3; and FIG. 9 is a sectional side elevation of modification of the embodiment shown in FIG. 3.

DESCRIPTION OF THE PREFERRED EMBODIMENTS

Figure 1:
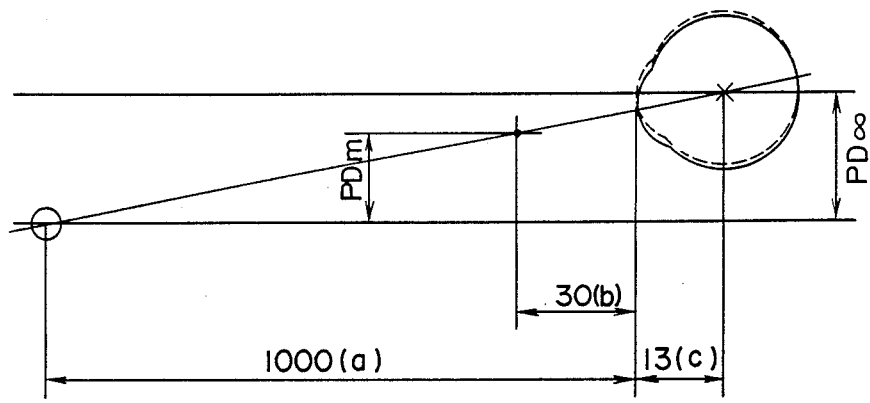
FIGS. 1 and 2 are illustrations explanatory of the principle of the pupillary distance measuring device in accordance with the present invention.
Figure 2:
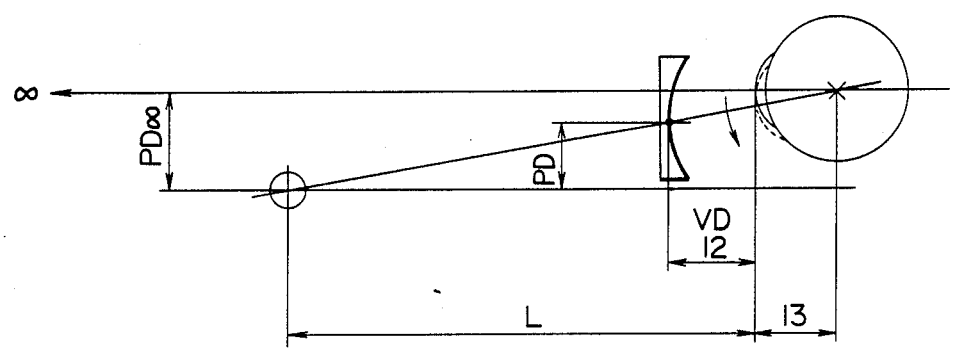

Referring to the drawings, fixation target illuminating light sources 1a and 1b for right and left eyes are arranged to illuminate dot-like fixation targets 2a, 2b which are adhered to the front side of condenser lenses 21a and 21b.

The pupillary distance measuring device of the present invention does not incorporate each light shield plate which is usually used for shielding one of two eyes. Measurement of each eye is made possible by selectively turning on and off one of the illuminating light sources 1a and 1b for right and left eyes.

In case of mounting a fixation target for common use to both eyes, it is necessary to enable to insert into the light axis the light shield plate for shielding one of eyes.

A reference numeral 3 denotes a total reflection mirror. The arrangement is such that the optical axis of the fixation target and the optical axis of observation of the inspector are slightly discrepant from each other in the vertical direction. Obviously, it is possible to arrange such that both optical axes coincide with each other, provided that a half mirror is used in place of the total reflection mirror, though the light quantity is reduced almost to a half value. (see FIGS. 8 and 9)

Figure 7:
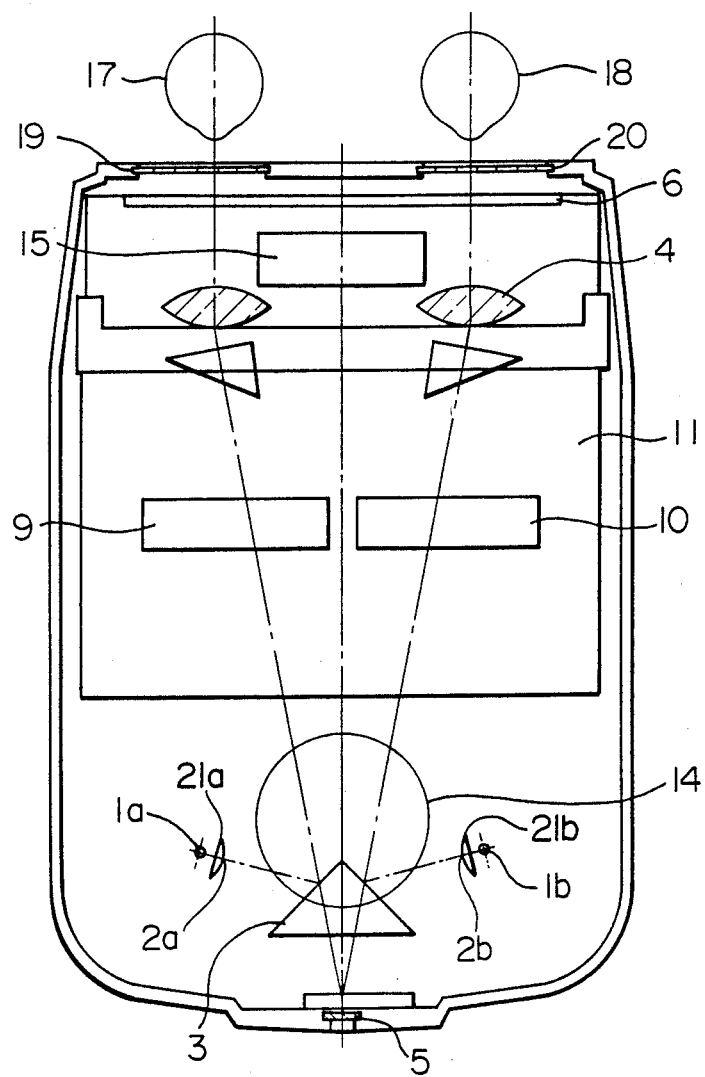
FIG. 7 is a sectional view of a modification of the embodiment shown in FIG. 3.

The focal distance and the position of an objective lens 4 are so determined that the fusion of the fixation target can easily be formed. Namely, the illustrated embodiment is designed such that the viewing distance is 1 m. Since the objective lens is immovable, it is easy to arrange each objective lens for the right and left eyes. Whether a pair of objective lenses for both eyes or a single objective lens is used is a matter of design and production technic. (see FIG. 7)

An eyepiece 5 enables the inspector to observe a cornea reflection image (bright spot) formed on the cornea of the subject.

A liquid crystal display unit (LCD) 6 of light-transmitting type is disposed at a distance of 30 mm from the vertex of the cornea of the subject. The distance value of 30 mm is not critical but it is significant that the distance is known.

Figure 5:
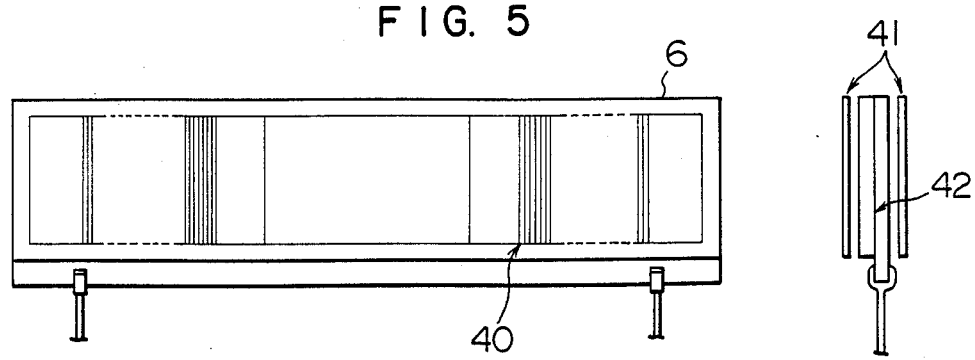
FIG. 5 is an illustration of the shape and construction of a liquid crystal display incorporated in the embodiment of FIG. 3.

FIG. 5 shows the shape and construction of a liquid crystal display 6. As will be seen from this Figure, the liquid-crystal display unit 6 used in this embodiment is a segment type unit because the object of the device is limited to the collection of data necessary for setting a spectacles lens in a spectacles frame in respect of facility to operate the unit. Each segment 40 is formed by conducting photo-etching on glass coated with a transparent metal coating layer and, hence, exhibits a high degree of precision. Numerals 41 and 42 denote a polarizing plate and a liquid crystal which are essential portions of the liquid-crystal display unit 6. When a voltage is applied to one of the segments 40, the segment 40 becomes opaque so that a black line (referred to as "hair-line pattern) is displayed.

Obviously, the liquid crystal display unit 6 may be of a matrix type as shown in the specification of the U.S. Pat. No. 4,591,246. In such a case, it is not necessary to use the hair-line pattern.

The hair-line pattern is progressively movable to the left and right by an amount proportional to a value input to a microcomputer 15, the input being obtained through an A/D conversion of output voltages derived from linear potentiometers 9 and 10.

The pupillary distance measuring knobs 7 and 8 are operatively connected to linear potentiometers 9 and 10 respectively so that these linear potentiometers are capable of outputting voltages proportional to the amount of operation of the pupillary distance measuring knobs 7 and 8.

The microcomputer 15 and a liquid-crystal display unit 12 for displaying the results of computation are mounted in a circuit board 11, together with other components.

A viewing distance setting knob 13 is directly connected to the potentiometer 14. Read switch 16 is the switch for inputting to the microcomputer the voltage signal of linear potentiometer, which signal is A/D converted. When the hair-line pattern has coincided with the cornea reflection image of the fixation target, the inspector pushes the switch 16 so that the A/D converted voltage signal, corresponding to that position of the hairline pattern, is input to the microcomputer.

Numerals 17 and 18 denote right and left eyes of a subject, which are protected by protective glasses 19 and 20.

Figure 6:
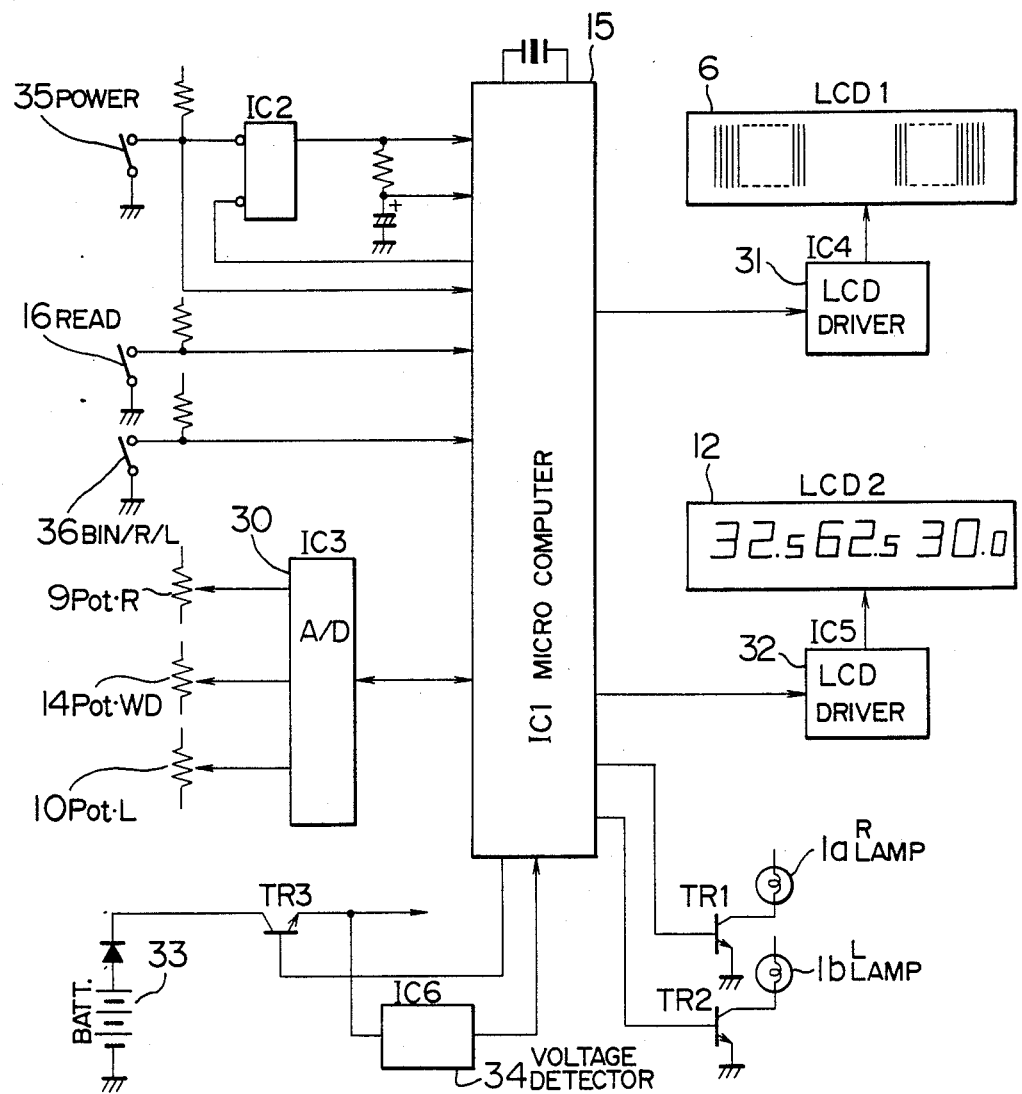
FIG. 6 is a block diagram of an electrical system in the embodiment shown in FIG. 3.

As shown in FIG. 6, the electric circuit incorporated in the pupillary distance measuring device of this embodiment includes an A/D converter 30 for conducting A/D conversion of outputs from the linear potentiometers 9 and 10, liquid-crystal display (LCD) drivers 31 and 32, a battery 33 and a battery voltage detector (VOLTAGE DETECTOR) 34. The electric circuit further includes a power supply switch 35, and a select switch 36 for enabling selection of the inspection mode between a both-eyes inspection mode in which both the right and left eyes are inspected and a single-eye inspection mode in which either the right or left eye is inspected. The illumination light sources la and lb are turned on and off in accordance with the state of this select switch 36.

Though the sighting mark to positioned in relation to the bright spot is constituted by a liquid-crystal unit, this is only illustrative and the arrangement may be such that the sighting mark is formed of a hairly thin bar which is mechanically movable accompanied by a brush slidable on an encoder so that the required information is derived from the encoder.

What is claimed is:

1. A device for measuring a pupillary distance comprising:
    fixation target forming means disposed in said device and including at least a light source;
    a window provided in a front panel of said device in such a manner as to enable a subject to look at a fixation target in the device;
    locating means for locating said front panel properly in relation to a face of said subject;
    at least a converging lens fixedly mounted in said device such that an appearant viewing distance of said fixation target has a predetermined distance value and said converging lens is disposed corresponding to at least one eye of the subject;
    sighting mark forming means provided on an inner side of said front panel such as to form a sighting mark which corresponds to a position of a cornea reflection image of said fixation target formed on a cornea of said subject;
    sighting mark position control means for enabling an inspector to control a position of said sighting mark in relation to the position of said cornea reflection image;
    observation means for enabling said inspector to observe a front portion of an eye of said subject;
    sighting mark position reading means for reading a position of said sighting mark at least at a preselected viewing distance;
    viewing distance setting means for setting a viewing distance at which said pupillary distance is desired to be determined;
    computing means for determining the pupillary distance at the desired viewing distance set by said viewing distance setting means based upon the position of said sighting mark at said preselected viewing distance; and
    computing display means for displaying the result of said means.

2. A pupillary distance measuring device according to claim 1, wherein the apparent viewing distance of said fixation target is set at a short distance which enables an easy forming of a fusion.

3. A pupillary distance measuring device according to claim 2, wherein said appearent viewing distance ranges between about 1m and 2m.

4. A pupillary distance measuring device according to claim 2, wherein said sighting mark forming means includes a light-transmitting type liquid-crystal display unit.

5. A pupillary distance measuring device according to claim 4, wherein said light-transmitting type liquid crystal display unit is of segment type having a plurality of line-shaped segments.

6. A pupillary distance measuring device according to claim 1, wherein said fixation target forming means is used commonly both for right and left eyes.

7. A pupillary distance measuring device according to claim 1, wherein said fixation target forming means is provided independently for each of right and left eyes.

8. A pupillary distance measuring device according to claim 1, wherein said sighting mark is a hair-like thin bar which is movable mechanically.

9. A pupillary distance measuring device according to claim 1, wherein said sighting mark position reading means includes a linear potentiometer.

10. A pupillary distance measuring device according to claim 1, wherein said viewing distance setting means includes a rotary potentiometer.

11. A pupillary distance measuring device according to claim 1, wherein a computation of said pupillary distance at said desired viewing distance with a signal output from said sighting mark position reading means is determined by said computing means in accordance with a formula:

$$PD = PDm \times \frac{(a + c)}{(a - b)} \times \frac{(L - VD)}{(L + c)}$$

where PD is the pupillary distance at the desired viewing distance, PDm is a pupillary distance at said preselected viewing distance, a is a preselected viewing distance, b is a distance between the sighting mark and a top of the cornea, c is a distance from a vertex of a cornea to a rotation center of the corner, L is the desired viewing distance at which said pupillary distance is to be determined and VD is vertex distance.

* * * * *